(12) United States Patent
Solek

(10) Patent No.: US 11,364,010 B2
(45) Date of Patent: *Jun. 21, 2022

(54) PORTABLE ULTRASOUND IMAGING PROBE INCLUDING A TRANSDUCER ARRAY

(71) Applicant: INTERSON CORPORATION, Pleasanton, CA (US)

(72) Inventor: Roman Solek, Pleasanton, CA (US)

(73) Assignee: INTERSON CORPORATION, Pleasanton, CA (US)

( * ) Notice: Subject to any disclaimer, the term of this patent is extended or adjusted under 35 U.S.C. 154(b) by 212 days.

This patent is subject to a terminal disclaimer.

(21) Appl. No.: 16/692,052

(22) Filed: Nov. 22, 2019

(65) Prior Publication Data

US 2020/0100766 A1    Apr. 2, 2020

Related U.S. Application Data

(63) Continuation of application No. 13/951,807, filed on Jul. 26, 2013, now Pat. No. 10,499,878.

(Continued)

(51) Int. Cl.
*A61B 8/00* (2006.01)
*A61B 8/14* (2006.01)
(Continued)

(52) U.S. Cl.
CPC ............ *A61B 8/4494* (2013.01); *A61B 8/145* (2013.01); *A61B 8/4427* (2013.01); *A61B 8/4444* (2013.01); *A61B 8/461* (2013.01); *A61B 8/52* (2013.01); *A61B 8/54* (2013.01); *A61B 8/56* (2013.01); *B06B 1/0215* (2013.01); *B06B 1/0622* (2013.01); *G01S 7/52079* (2013.01); *G01S 15/8915* (2013.01);
(Continued)

(58) Field of Classification Search
CPC ... A61B 8/4494; A61B 8/4444; A61B 8/4427; G01S 15/8927; G01S 7/5208
See application file for complete search history.

(56) References Cited

U.S. PATENT DOCUMENTS

| 4,140,022 A | 2/1979 | Maslak |
| 4,159,462 A | 6/1979 | Rocha |

(Continued)

FOREIGN PATENT DOCUMENTS

WO    2005038449    4/2005

OTHER PUBLICATIONS

Wygant, Ira O, et al., "Integration of 2D CMUT Arraays with Front-End Electronics for Volumetric Ultrasound Imaging", IEEE Transactions On Ultrasonics, Ferroelectrics, and Frequency Control., vol. 55, No. 2, Feb. 2008, 327-342.

(Continued)

*Primary Examiner* — Amelie R Davis
(74) *Attorney, Agent, or Firm* — Tucker Ellis LLP

(57) ABSTRACT

A portable ultrasonic imaging probe that is adapted to connect to a host computer via a passive interface cable. The probe includes an array of ultrasound transducers, a high voltage pulser for energizing transducers to emit an ultrasound pulse, analog signal processing circuitry that combines echoes detected by transducers into a single analog echo signal, am analog-to-digital converter that converts the analog echo signal into a digital echo signal; and interface circuitry that transfers the digital echo signal across the passive interface cable to the host computer.

26 Claims, 6 Drawing Sheets

Related U.S. Application Data

(60) Provisional application No. 61/676,193, filed on Jul. 26, 2012.

(51) Int. Cl.
    *A61B 8/08*     (2006.01)
    *G01S 7/52*     (2006.01)
    *G01S 15/89*     (2006.01)
    *B06B 1/06*     (2006.01)
    *B06B 1/02*     (2006.01)

(52) U.S. Cl.
    CPC ....... *G01S 15/8927* (2013.01); *B06B 2201/51* (2013.01); *B06B 2201/55* (2013.01); *B06B 2201/76* (2013.01)

(56) References Cited

U.S. PATENT DOCUMENTS

| | | | |
|---|---|---|---|
| 4,530,363 | A | 7/1985 | Brisken |
| 4,589,284 | A | 5/1986 | Breimesser |
| 4,773,426 | A | 9/1988 | Molnar |
| 4,953,147 | A | 8/1990 | Cobb |
| 5,369,890 | A | 12/1994 | Malz |
| 5,394,750 | A | 3/1995 | Matzuk |
| 5,563,346 | A | 10/1996 | Bartelt |
| 5,613,493 | A | 3/1997 | Schafer |
| 5,647,367 | A | 7/1997 | Lum |
| 5,795,297 | A | 8/1998 | Daigle |
| 5,840,032 | A | 11/1998 | Hatfield |
| 5,913,447 | A | 6/1999 | Carpenter |
| 6,012,332 | A | 1/2000 | Schafer |
| 6,013,032 | A | 1/2000 | Savord |
| 6,045,508 | A | 4/2000 | Hossack |
| 6,099,474 | A | 8/2000 | Solek |
| 6,113,545 | A | 9/2000 | Chiao |
| 6,120,454 | A | 9/2000 | Suorsa |
| 6,213,948 | B1 | 4/2001 | Barthe |
| 6,238,346 | B1 | 5/2001 | Mason |
| 6,381,197 | B1 | 4/2002 | Savord |
| 6,398,734 | B1 | 6/2002 | Cimochowski |
| 6,440,071 | B1 | 8/2002 | Slayton |
| 6,458,073 | B1 | 10/2002 | Bonthuys |
| 6,524,244 | B1 | 2/2003 | Knell |
| 6,595,921 | B1 | 7/2003 | Urbano |
| 6,719,693 | B2 | 4/2004 | Richard |
| 6,865,140 | B2 | 3/2005 | Thomenius |
| 6,887,204 | B2 | 5/2005 | Nozaki |
| 6,969,352 | B2 | 11/2005 | Chiang |
| 6,974,417 | B2 | 12/2005 | Lockwood |
| 7,484,412 | B2 | 2/2009 | Hart |
| 7,489,593 | B2 | 2/2009 | Nguyen-Dinh |
| 7,673,479 | B2 | 3/2010 | Dahlheimer |
| 8,114,024 | B2 | 2/2012 | Solek |
| 8,500,641 | B2 | 8/2013 | Raju |
| 10,499,878 | B2 | 12/2019 | Solek |
| 2003/0028109 | A1 | 2/2003 | Miller |
| 2003/0045794 | A1 | 3/2003 | Bae |
| 2004/0015079 | A1 | 1/2004 | Berger |
| 2004/0195778 | A1 | 10/2004 | Smith |
| 2005/0228281 | A1 | 10/2005 | Nefos |
| 2006/0145426 | A1 | 7/2006 | Schroeder |
| 2007/0239019 | A1 | 10/2007 | Richard |
| 2008/0255451 | A1 | 10/2008 | Cohen |
| 2008/0300490 | A1 | 12/2008 | Chiang |
| 2011/0295119 | A1 | 12/2011 | Miller |
| 2014/0031693 | A1 | 1/2014 | Solek |
| 2014/0031694 | A1 | 1/2014 | Solek |
| 2015/0216511 | A1 | 8/2015 | Tur |
| 2015/0241397 | A1 | 8/2015 | Savord |
| 2017/0343655 | A1 | 11/2017 | Solek |

OTHER PUBLICATIONS

Angelsen, Bjorn A.J., et al., "Which transducer array is best?", European Journal of Ultrasound 2 (1995) 151-164.

AD8310 Datasheet, "Fast, Voltage-Out DC-440 MHz, 95 dB Logarithmic Amplifier," Analog Devices, Inc. (2005), http://www.analos.com/UploadedFileslData Sheets181 5636058AD8310 e.pdf.

EZ-USB FX2LP USB Microcontroller Datasheet, Cypress Semiconductor Corporation (2005), http://fp.cse.wustl.edu/cse462/Downloads/c7c68013a 5.pdf.

Johnson, Jeremy et al., "Medical imaging using capacitive micromachined ultrasonic transducer arrays", Ultrasonics 40 (2002) 471-476.

Johnson, Jeremy et al., "Coherent-Array Imaging Using Phased Subarrays. Part I: Basic Principles", IEEE Transactions on Ultrasonics, Ferroelectrics, and Frequency Control, vol. 52, No. 1, Jan. 2005 (37-50).

Khuri-Yakub, Butrus et al., "Next-Gen Ultrasound", spectrum.ieee.org. Retrieved Jul. 12, 2012, from http://spectrum.ieee.org/biomedical/imaging/nextgen-ultrasound/0.

Khuri-Yakub, B. (Pierre) T., "MEMS based ultrasonic transducers in medical imaging, therapy and sensing", parc.com. Retrieved Jul. 12, 2012 from http://www.parc.com/event/642/mems-based-ultrasonic-transducers-in-medical-imaging-therapy-and-se nsing.html.

Richard, W.D., "A New Time-Gain Correction Method for Standard B-Mode Ultrasound Imaging," IEEE Transactions on Medical Imaging, vol. 8, pp. 283-285, Sep. 1989.

Richard, W.D. and R.M. Arthur, "Real-Time Ultrasonic Scan Conversion via Linear Interpolation of Oversampled Vectors," Ultrasonic Imaging, vol. 16, pp. 109-1 23, Apr. 1994.

Richard, W.D., et al., "A Low-cost B-Mode USB Ultrasound Probe", Ultrasonic Imaging, vol. 30, 9 pages, 2008.

Seagar, Andrew Dr., "Basic Principles of Ultrasound Imaging System Design", Biomedical Imaging HET408, Mar. 25, 2002, 22 pages.

Nguyen-Dinh, An, "From MEMS devices to Medical Diagnostic Market. A case study: Ultrasonic Imaging", Mar. 2011, Presentation by An Nguyen-Dinh, Director of Technology, Vermon SA, France, 20 pages.

Wong, Serena H. et al., "Evaluation of Wafer Bonded CMUTs with Rectangular Membranes Featuring High Fill Factor", IEEE Transactions On Ultrasonics, Ferroelectrics and Frequency Control, vol. 55, No. 9, Sep. 2008, 2053-2065.

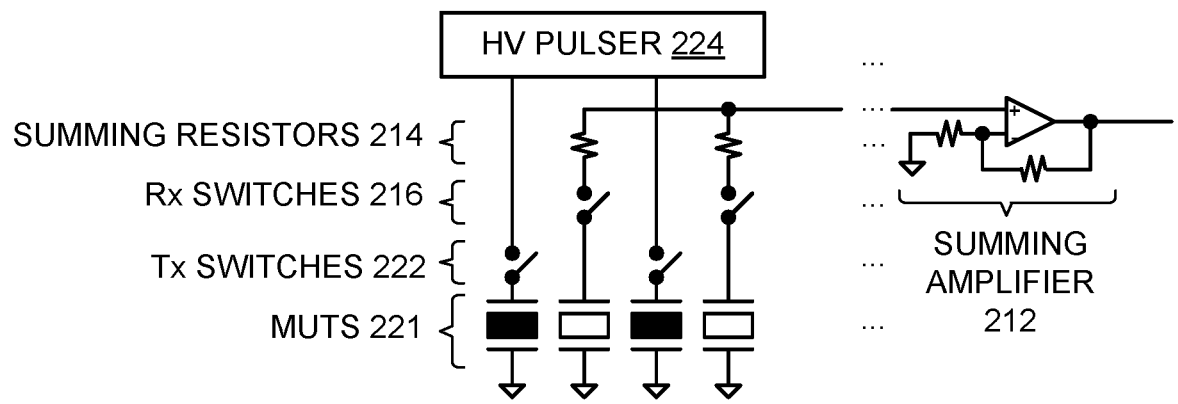
FIG. 2B
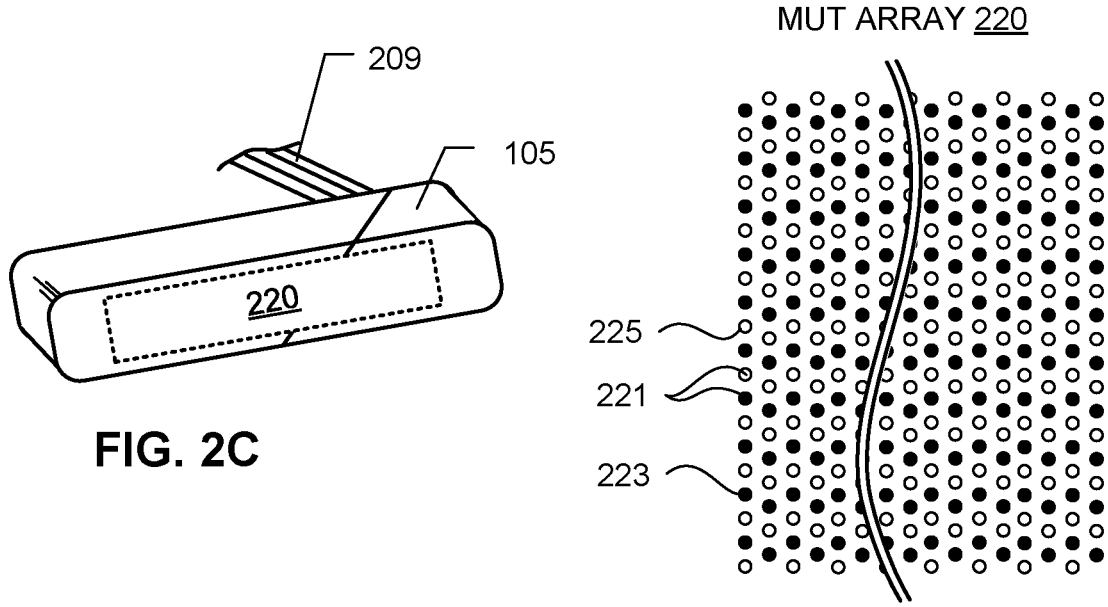
FIG. 2C
FIG. 2D

FIG. 3A
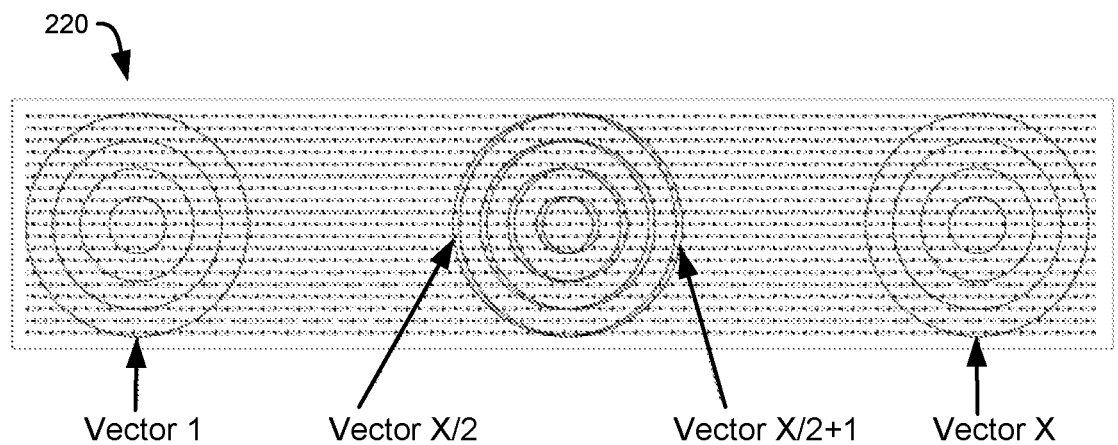
Vector 1    Vector X/2    Vector X/2+1    Vector X
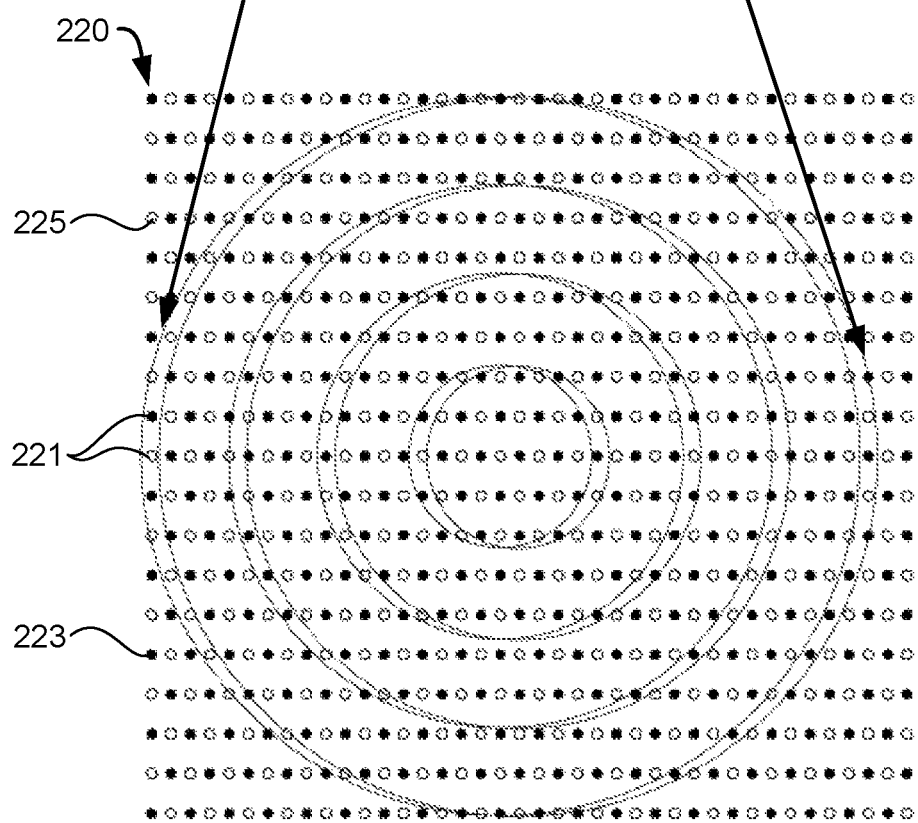
FIG. 3B

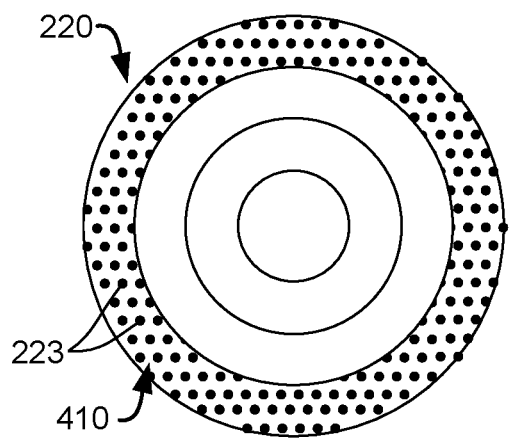
(a) Transmit 1
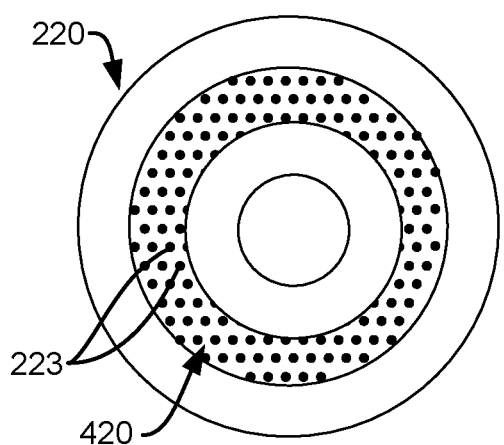
(b) Transmit 2
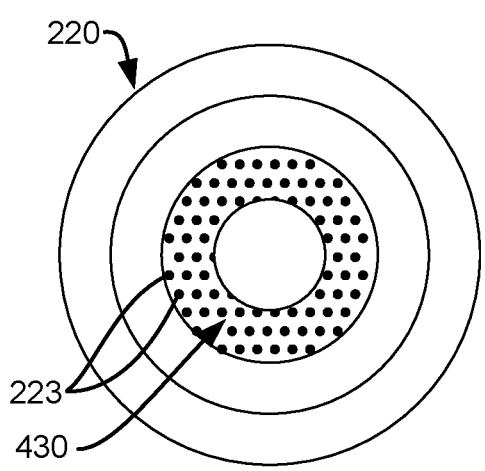
(c) Transmit 3
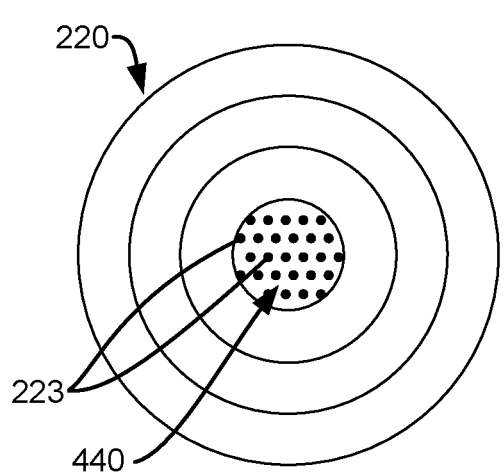
(d) Transmit 4

(a) Receive 1

(b) Receive 2

(c) Receive 3

(d) Receive 4

PORTABLE ULTRASOUND IMAGING PROBE INCLUDING A TRANSDUCER ARRAY

PRIORITY CLAIM

This application is a continuation of U.S. patent application Ser. No. 13/951,807 entitled "PORTABLE ULTRASONIC IMAGING PROBE INCLUDING A TRANSDUCER ARRAY" filed Jul. 26, 2013 which claims the benefit of priority to U.S. Provisional Patent Application No. 61/676,193 filed Jul. 26, 2012 entitled "PORTABLE ULTRASONIC IMAGING PROBE INCLUDING MEMS BASED TRANSDUCER ARRAY", both of which applications are incorporated herein by reference.

FIELD OF THE INVENTION

The present invention relates to portable ultrasonic imaging probes, and more specifically, to such probes including transducer array, wherein such probes can be directly connected to a host computer, such as an off-the-shelf laptop computer, or the like.

BACKGROUND

Typically, ultrasound imaging systems include a hand-held probe that is connected by a cable to a relatively large and expensive piece of hardware that is dedicated to performing ultrasound signal processing and displaying ultrasound images. Such systems, because of their high cost, are typically only available in hospitals or in the offices of specialists, such as radiologists. Recently, there has been an interest in developing more portable ultrasound imaging systems that can be used with personal computers. Preferably, such a portable ultrasound probe can be used with an off-the-shelf host computer, such as a personal computer, and is inexpensive enough to provide ultrasound imaging capabilities to general practitioners and health clinics having limited financial resources.

BRIEF DESCRIPTION OF THE DRAWINGS

FIG. 2B illustrates some further details of some of the blocks introduced in FIG. 2A, according to an embodiment of the present invention.

FIG. 2C illustrates a perspective view of a probe head assembly, according to an embodiment of the present invention.

FIG. 2D illustrates how odd and even rows can be staggered relative to one another.

FIG. 3A is used to illustrate how sets of micromachined ultrasound transducers (MUTs) that collectively make up rings can be used to form a quasi-annular array transducer, and that such rings can be moved to emulate the mechanical movement of an annular array transducer, without requiring any moving parts.

FIG. 3B is a blown-up view of two of the vectors shown in FIG. 3A.

FIGS. 4A-4D are used to illustrate a transmit sequence, according to an embodiment of the present invention.

DETAILED DESCRIPTION

Figure 1A:
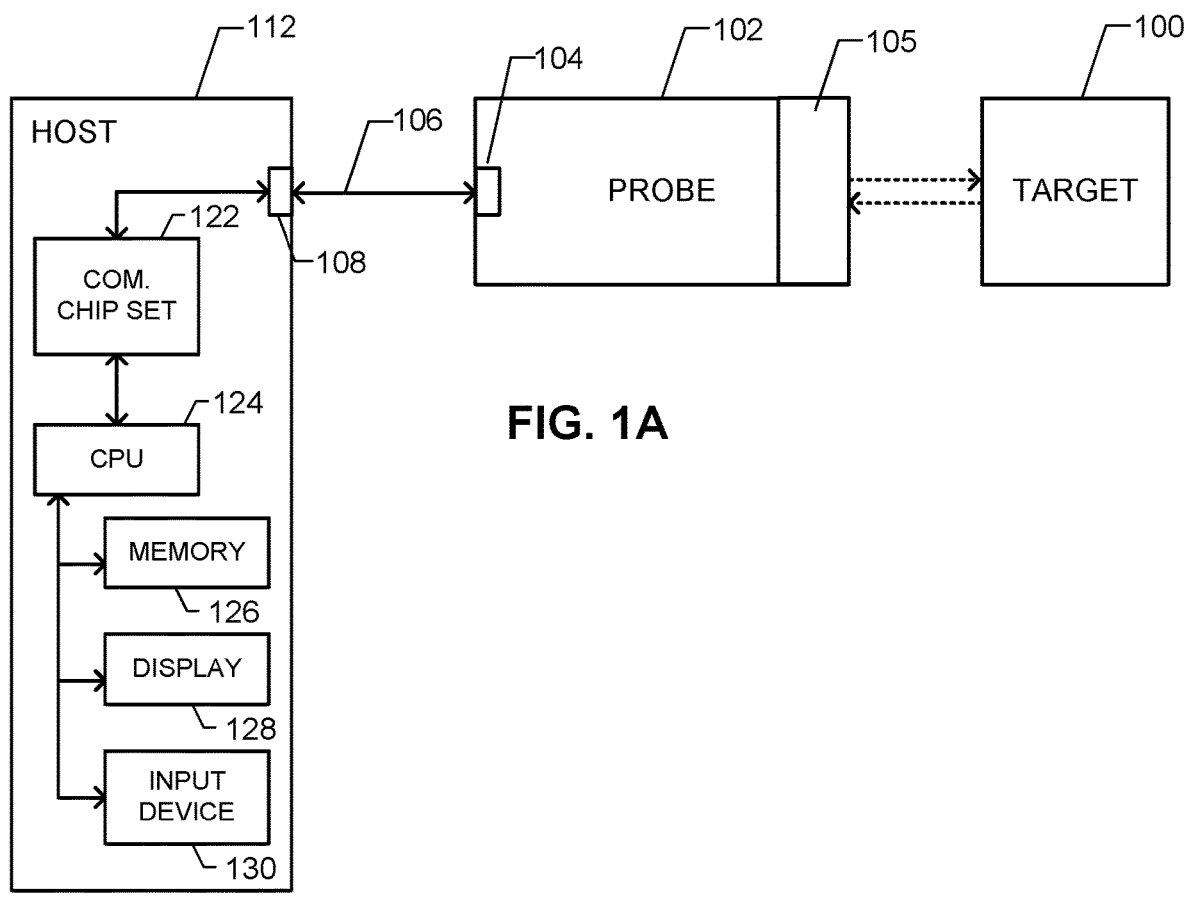
FIG. 1A is a high level diagram that is useful for describing embodiments of the present invention.

In the following detailed description, reference is made to the accompanying drawings that form a part hereof, and in which is shown by way of illustration specific illustrative embodiments. It is to be understood that other embodiments may be utilized and that mechanical and electrical changes may be made. The following detailed description is, therefore, not to be taken in a limiting sense. In the description that follows, like numerals or reference designators will be used to refer to like parts or elements throughout. In addition, the first digit of a reference number identifies the drawing in which the reference number first appears.

FIG. 1A shows an ultrasonic imaging probe 102, according to an embodiment of the present invention, which is connected by a passive interface cable 106 to a host computer 112. Ultrasonic imaging probe 102 includes an array of ultrasound transducers for transmitting and receiving ultrasound pulses as will be described below. The host computer 112 can be a desktop personal computer (PC), a laptop PC, a pocket PC, a tablet PC, a mobile phone capable or running software programs (often referred to as a "smart phone"), a personal digital assistant, or the like. The passive interface cable 106, which includes connectors and passive wires, can be a Universal Serial Bus (USB) cable (e.g., a USB 2.0 cable), a FireWre (also known as IEEE 1394) cable, or the like. Preferably the probe 102 is not connected to any other device or power supply. Thus, in a preferred embodiment the probe 102 receives all its necessary power from the host computer 112 via the passive interface cable 106. In alternative embodiments, probe 102 can include a battery and a wireless transceiver, in which case the probe can wireless communicate with the host computer, and the probe can generate all its necessary power from the battery.

As will be described in more detail below, in accordance with embodiments of the present invention, the probe 102 enables the host computer 112, via software running on the host computer 112, to form real-time ultrasonic images of a target 100 (e.g., human tissue or other materials) without the need for any additional internal or external electronics, power supply, or support devices. In certain embodiments, the probe 102 produces raw digitized data that is envelope detected ultrasound echo data from an array of micromachined ultrasound transducers (MUTs) in the probe 102, and transmits such raw data to the host computer 112. The raw digitized data can optionally also be logarithmically compressed, depending upon implementation. In an embodiment, when the host computer 112 receives raw data via the passive interface cable 106 from the probe 102, the host computer 112 performs time gain compensation (TGC), gray-scale mapping, and scan conversion of the raw data using software that runs on the host computer 112, and displays the resultant video images. The probe does not include any moving mechanical parts, thereby reducing the complexity and cost of the probe 102 and increasing its reliability. The term "raw data", as used herein, refers to ultrasound imaging data that has not yet been time gain compensated, gray-scale mapped and scan converted. As described below, such raw data is included in the digital signal that is transferred from the probe 102 to the host computer 112.

As shown in FIG. 1A, the host computer 112 will likely include a communications port 108, a communications chip-set 122, a central processing unit (CPU) 124, memory 126, a display 128, and an input device 130, such as a keyboard, mouse, touch screen, track ball, or the like. Additionally, the host computer 112 runs software that enables the host to control specific aspects of the probe 102. Such software also enables the host computer 112 to perform time gain compensation (also known as time gain correction), gray-scale mapping, and scan conversion of the raw data received from the probe 112 over the passive interface cable 106. The host computer 112 can then display the resulting ultrasound video on the display 128, as well as store such video in its memory 126, or another data storage device (not shown). The article "A New Time-Gain Correction Method for Standard B-Mode Ultrasound Imaging", by William D. Richard, *IEEE Transactions of Medical Imaging*, Vol. 8, No. 3, pp. 283-285, September 1989, which is incorporated herein by reference, describes an exemplary time gain correction technique that can be performed by the host computer 112. The article "Real-Time Ultrasonic Scan Conversation via Linear Interpolation of Oversampled Vectors," *Ultrasonic Imaging*, Vol. 16, pp. 109-123, April 1994, which is incorporated herein by reference, describes an exemplary scan conversion technique that can be performed by the host computer 112. These are just exemplary details of the host computer 112, which are not meant to be limiting.

The passive interface cable 106 includes at least one data line over which data is carried, and at least one power line to provide power to a peripheral device, which in this case is the ultrasonic imaging probe 102. For example, where the passive interface cable 106 is a USB 2.0 cable, one wire of the cable provides about 5V at about ½ Amp. In alternative embodiments, the passive interface cable 106 is a Firewire cable, which also includes a power wire. Other types of passive interface cable can be used if desired. However, as mentioned above, it is preferred that the passive interface cable 106 is a standard off-the-shelf cable that can interface with an off-the-shelf interface IC. The term passive as used herein refers to a cable that does not regenerate signals or process them in any way. In an alternative embodiment, the probe 102 and the host computer 112 communicate wirelessly, and the probe 102 includes a battery that is used to power the components within the probe.

Figure 1B:
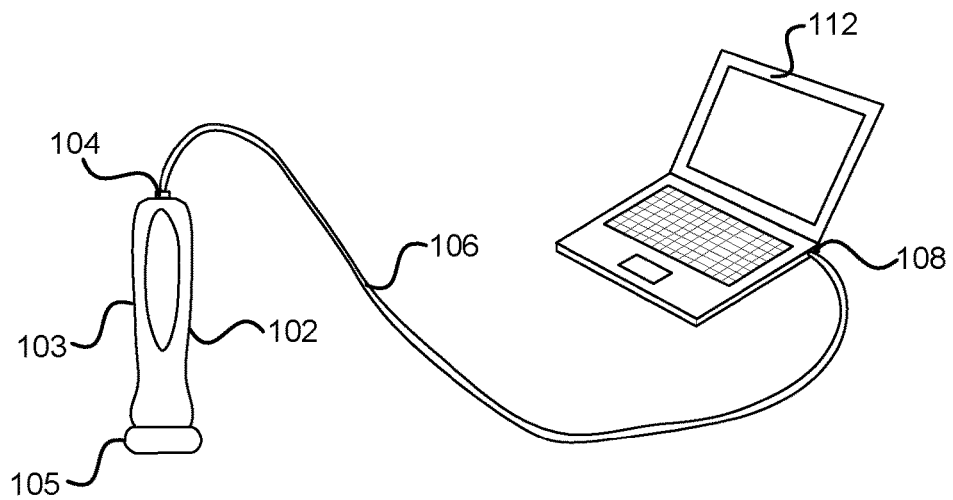
FIG. 1B illustrates a specific implementation of the invention originally described with reference to FIG. 1A.

FIG. 1B illustrates an example where the host computer 112 is a laptop. FIG. 1B also shows an exemplary ergonomic design of a housing 103 for the ultrasonic imaging probe 102 of the present invention. Other ergonomic designs are of course possible, and within the scope of the present invention. Also, as explained above, other types of host computer 112 can also be used. FIG. 1B also shows that the ultrasonic imaging probe 102 includes a probe head assembly 105.

In accordance with certain embodiments, the data samples produced by the ultrasound imaging probe 102 of the present invention are transmitted by the probe 102 across the interface cable 106 to the host computer 112. In a specific embodiment, this is accomplished when the host computer 112 reads the data temporarily stored in the buffers of the interface IC 204. The host computer 112 runs software that enables the host to perform time gain compensation (TGC), gray-scale mapping, and scan conversion of the data received from the probe 102, and the host displays the resultant video images. Advantageously, the host computer 112 does not need to perform electronic beamforming or other equivalent image processing, thereby simplifying the software that the host computer 112 runs.

The host computer 112 can use the digital data received from the ultrasound device 102 to provide any available type of ultrasound imaging mode can be used by the host computer 112 to display the ultrasound images, including, but not limited to A-mode, B-mode, M-mode, etc. For example, in B-mode, the host computer 112 performs know scan conversion such that the brightness of a pixel is based on the intensity of the echo return.

A benefit of specific embodiments of the present invention is that only digital signals are transmitted from the probe 102 to the host computer 112, thereby providing for better signal-to-noise ratio than if analog signals were transmitted from the probe 102 to the host computer 112, or to some intermediate apparatus between the host computer and the probe. Another benefit of specific embodiments of the present invention is that the probe 102 can be used with a standard off-the-shelf passive interface cable.

A further benefit of specific embodiments of the present invention is that the probe 102 does not perform any time gain compensation, gray-scale mapping and scan conversion, thereby significantly decreasing the complexity, power requirements and cost of the probe 102. Conventionally, functions such as scan conversion, time gain correction (also known as time gain compensation) and gray-scale mapping are performed by a machine that is dedicated to obtaining ultrasound images, or by an intermediate device that is located between the probe and host computer. In contrast, here software running on the host computer 112 is used to perform these functions, thereby reducing the complexity and cost of the portable ultrasonic imaging probe 102.

Figure 2A:
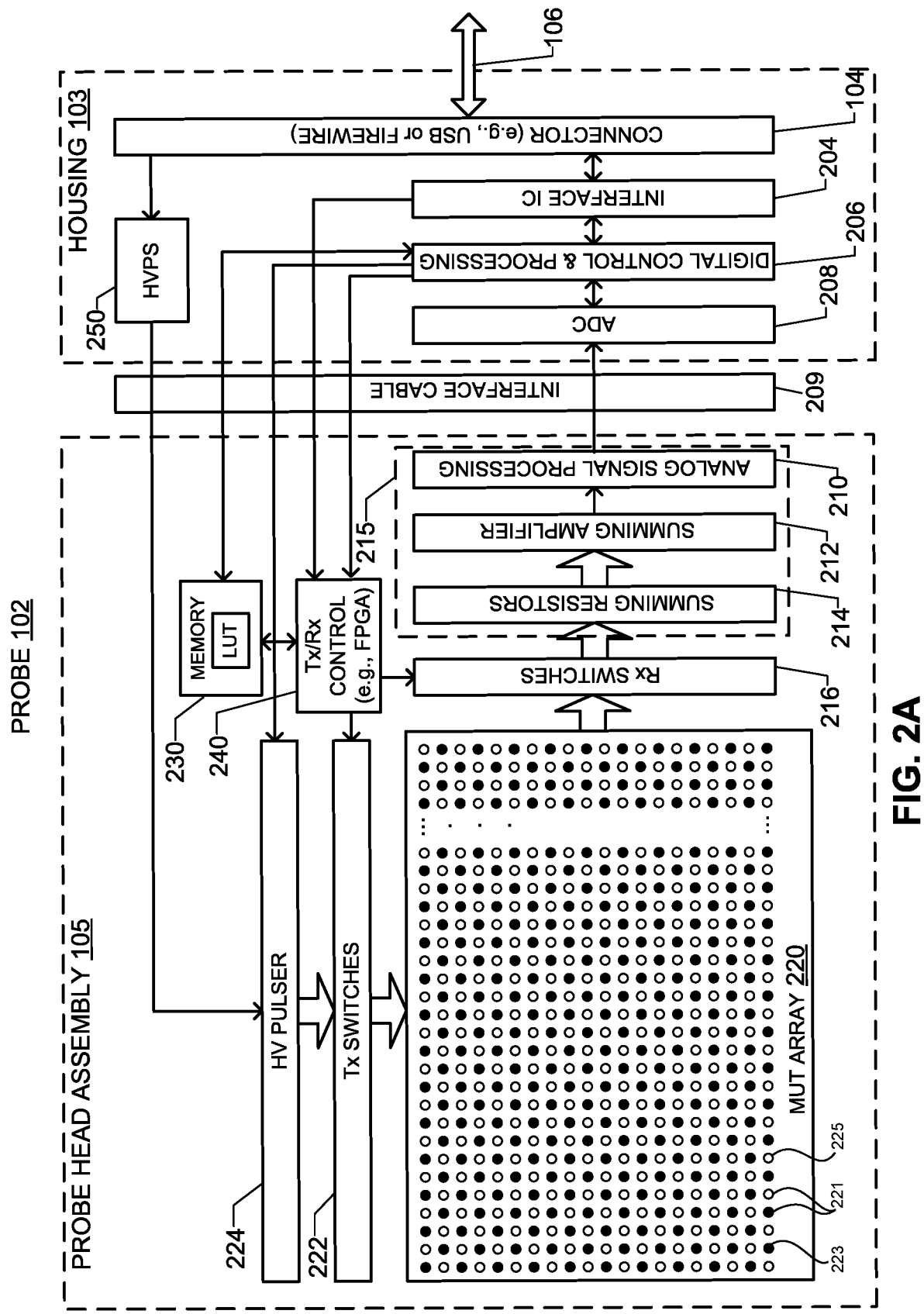
FIG. 2A is a block diagram that shows additional details of an ultrasonic imaging probe according to an embodiment of the present invention.

FIG. 2A is a block diagram that shows additional details of an ultrasonic imaging probe according to an embodiment of the present invention. Additional details of the ultrasonic imaging probe 102, according to specific embodiments of the present invention, shall now be described with reference FIG. 2A. As shown in FIG. 2A, in accordance with an embodiment of the present invention, the probe 102 includes a peripheral connector 104 and an interface IC 204 that enables the probe 102 to interface with the host computer 112 via the interface cable 106. The connector 104 and the interface IC 204 are preferably off-the-shelf devices, but can be custom devices.

In accordance with an embodiment illustrated in FIG. 2A, specific certain components (shown within a large dash-lined rectangle) are located within the probe head assembly 105, with the remaining components being within the housing 103 of the ultrasonic imaging probe 102. An interface cable 209 connects the components within the housing 103 to the components within the probe head assembly 105.

The probe 102 is also shown as including a digital control and processing block 206, an analog to digital converter (ADC) 208 and a high voltage power supply (HVPS) 250. The HVPL 250 provides power to a high voltage (HV) pulser 224. Additionally, the probe 102 is shown as including a micromachined ultrasound transducer (MUT) array 220, which includes individually controllable MUT elements 221, which are discussed in additional detail below. A transmit and receive (Tx/Rx) controller 240 accesses vector configuration and timing data stored within a memory 230 in order to controls transmit (Tx) switches 222 and receive (Rx) switches 216, to thereby control the operation of the MUT elements 221 of the array 220, as described in additional detail below. In certain embodiments, such vector configuration and timing data is stored within a look-up table (LUT) within the memory 230.

The probe 102 also includes analog summing, amplification and processing circuitry 215. In accordance with an embodiment, the analog summing, amplification and processing circuitry 215 includes summing resistors 214 and a summing amplifier 212, which are discussed in more detail with reference to FIG. 2B, and an analog signal processing block 210. The analog signal processing block 210 can include, e.g., a pre-amplifier, a filter (e.g., a low pass or bandpass filter) and an envelope detector, and optionally a logarithmic amplifier. Such a pre-amplifier can be, e.g., a very low noise amplifier that provides about 20 dB of gain. The filter can filter out frequencies that are not of interest. The summing resistors 214 and the summing amplifier 212 combine numerous echo signals (received using numerous MUT elements) into a single echo signal. In accordance with an embodiment, this single echo signal is pre-amplified, filtered (e.g., low pass filtered) and envelope detected to produce a radio frequency (RF) signal. Logarithmic compression can be performed within the analog signal processing block 210, or within the digital control and processing block 210, or alternatively, within the host computer 112.

The RF signal output by the analog signal processing block 210 is digitized by the ADC 208. The ADC 208 samples the RF signal (e.g., at 30 or 48 MHz), to thereby digitize the signal, and provides the digitized signal to the digital control and processing block 210. The digital control and processing block 206 could be implemented, e.g., using a complex programmable logic device (CPLD), a field-programmable gate array (FPGA), an application specific integrated circuit (ASIC) or some other circuitry. The digital control and processing clock 206 control functions and timing of the hardware in the probe, and depending upon implementation, can also perform digital signal processing of the digital signal output by the ADC 208. For example, the digital control and processing block 206 can perform logarithmic compression, as was mentioned above. The digital control and processing clock 206 also controls the Tx/Rx controller 240.

The Tx/Rx controller 240, which can be implemented using an FPGA, an ASIC or some other circuitry, controls the Tx switches 222 so that a selected set of the MUTs transmit ultrasonic pulses generated by a high voltage (HV) pulser 224. The host computer 112, through the passive interface cable 106, and the interface IC 204 can control the amplitude, frequency and duration of the pulses output by the HV pulser 224. For example, the host computer 112 can write vector configuration and timing data to the memory 230. Additionally, the host computer 112 can send instructions to the probe 102 that cause the probe 102 to select, from the memory 230, specific transmit and receive vector control and timing data used to control transmission and reception of ultrasonic pulses.

The HV pulser 224 is powered by the HVPS 250, which generates the high voltage potential(s) required by the HV pulser 224 from a lower voltage (e.g., 5V) received via the passive interface cable 106. Depending upon implementation, the HV pulser 224 can produce unipolar pulses, or bipolar pulses. Unipolar pulses can be, e.g., high voltage pulses that are as large as 100V. Where the HV pulser 224 produces bipolar pulses, the HV pulser 224 may produce, e.g., both positive and negative high voltage pulses that can be as large as +/−100V. In such embodiments, the HVPS 250 can provide up to +/−100V supply rails to the HV pulser 224. Exemplary details of an HVPS, which can be used to implement the HVPS 250, are shown in and described with reference to FIG. 4 of U.S. Patent Publication No. 2007/0239019, which is incorporated herein by reference.

The probe 102 can also include a linear regulator IC (now shown) with integrated power switches and low quiescent current requirements designed for USB applications. For example, such a linear regular IC can produce a 3.3V digital supply and a 3.3V analog voltage supply, which are used to provide power to the various circuits/blocks within the probe 102. For example, a 3.3V digital supply can power the interface IC 204 and the digital control and processing block 206; and a 3.3V analog supply can power the summing amplifier 212 and the analog signal processing circuitry 210. An exemplary IC that can be used for the linear regulator IC is the TPS2148 3.3-V LDO and Dual Switch for USB Peripheral Power Management IC, available from Texas Instruments of Dallas, Tex.

Preferably, the probe 102 is configured as a single channel architecture, which means that only a single ADC 208 is required, and only a single data signal is transmitted from the probe 102 to the host 112 at any given time. However, in alternative embodiments, a multiple channel architecture that includes multiple ADCs can be implemented. Unless stated otherwise, the embodiments described herein include a single channel architecture.

Another benefit of specific embodiments of the present invention is that the MUT array 220 is in close proximity to (i.e., within the same housing as) the analog summing, amplifying and processing circuitry 215 and the ADC 208. This will provide for good signal-to-noise (S/N) ratio, as compared to systems where the analog signals output by the transducers must travel across a relatively long distance before they are amplified and/or digitized.

As mentioned above, the portable ultrasound imaging probe 102 includes a micromachined ultrasound transducer (MUT) array 220, which includes numerous MUTs 221, each of which can be referred to as an MUT element (or simply as an MUT). Such an MUT array 220, which can also be referred to as an array of MUTs, is an example of a MEMS based transducer, since the MUTs are examples of micro-electro-mechanical systems (MEMS). Each MUT element can include a single MUT cell, or multiple MUT cells hardwired together.

Each MUT cell can be a capacitive MUT (cMUT) cell or a piezoelectric MUT (pMUT) cell, but is not limited thereto. Such cells typically include a membrane (often referred to as a diaphragm) and two or more electrodes. For transmission, the electrodes and membrane are used to modulate a capacitive charge that vibrates the membrane and thereby transmits a sound wave. For reception, the electrodes and membrane are used to convert the sound vibration of a received ultrasound signal into a modulated capacitance. More specifically, when an AC signal is applied across the electrodes, the MUT generates ultrasonic waves in the medium of interest to thereby function as a transmitter. When ultrasonic waves are applied to the membrane of a MUT, the MUT generates an alternating signal as the capacitance of the MUT is varied to thereby function as a receiver of ultrasonic waves. Each MUT element can simply be referred to as an MUT, and a plurality of MUT elements can simply be referred to as MUTs. Preferably, the MUT array 220 is encased in material that has the proper acoustic impedance to be matched with acoustic impedance of human tissue.

Advantageously, MUTs can be made using semiconductor fabrication processes, such as microfabrication processes generally referred to as "micromachining". Micromachining is the formation of microscopic structures using patterning, deposition and/or etching. Patterning generally includes lithography, which can be performed using projection-aligners or wafer-steppers, but is not limited thereto. Deposition can be physical vapor deposition (PVD), chemical vapor deposition (CVD), low-pressure chemical vapor deposition (LPCVD), or plasma chemical vapor deposition (PECVD), but is not limited thereto. Etching can include wet-chemical etching, plasma-etching, ion-milling, sputter-etching or laser-etching, but is not limited thereto.

Micromachining is typically performed on substrates or wafers made of silicon, glass, sapphire or ceramic. Such substrates or wafers are generally very flat and smooth and have lateral dimensions in inches. They are usually processed as groups in cassettes as they travel from process tool to process tool. Each substrate can advantageously (but not necessarily) incorporate numerous copies of a product. Micromachining can include the use of conventional or known micromachinable materials including silicon, sapphire, glass materials of all types, polymers (such as polyimide), polysilicon, silicon nitride, silicon oxynitride, thin film metals such as aluminum alloys, copper alloys and tungsten, spin-on-glasses (SOGs), implantable or diffused dopants and grown films such as silicon oxides and nitrides, but is not limited thereto.

In accordance with an embodiment, the MUT array 220 includes M rows×N columns of transducer elements, with the MUTs 221 being illustrated as small circles in FIG. 2A. For example, if M=20 and N=100, then the MUT array would include 2000 MUTs. In accordance with an embodiment, half of the MUTs 221 can be selectively used for transmitting ultrasonic pulses, and the other half of the MUTs 221 can be selectively used for receiving "echo pulses". Continuing with the example where the MUT array 220 includes 2000 MUTs, then 1000 of the MUTs 221 can be can be selectively used for transmitting ultrasonic pulses, and 1000 of the MUTs 221 can be selectively used for receiving "echo pulses". More generally, P1 percent of the MUTs can be selectively used for transmitting ultrasonic pulses, and P2 percent (where P2=100%−P1) of the MUTs can be selectively used for receiving "echo pulses". Unless specified otherwise, it will be assumed that P1=P2=50%, such that half of the MUTs can be selectively used for transmitting ultrasonic pulses, and half of the MUTs can be selectively used for receiving "echo pulses".

For illustrative purposes, the MUTs that can be used for transmitting ultrasonic pulses, which can be referred to as Tx MUTs, are illustrated in FIG. 2A as small filled circles 223; and the MUTs that can be used for receiving ultrasonic pulses, which can be referred to as Rx MUTs, are illustrated in FIG. 2A as small unfilled circles 225.

Each of the MUTs 221 can have a circumferential shape that is circular, as shown. Each MUT 221 can be, e.g., about 50 micrometers in diameter, but is not limited thereto. The distance from the edge of one MUT 221 to its closest adjacent MUT 221 can be, e.g., about 70 micrometers, but is not limited thereto. Alternatively, each of the MUTs can have another circumferential shape, including, but not limited to, square or hexagonal. In accordance with certain embodiments, the Tx MUTs 223 and the Rx MUTs 225 are structurally the same. In such embodiments, the only difference between a Tx MUT 223 and an Rx MUT 225 is how the MUT is connected to other circuitry and used. In other embodiments, the Tx MUTs 223 can be structurally different from the Rx MUTs 225.

All of the rows and columns can be inline with one another, as shown in FIG. 2A. Alternatively, odd rows can be staggered relative even rows, as shown in FIG. 2D. It is also possible that odd columns be staggered relative to even columns. Other variations are also possible, and within the scope of an embodiment of the present invention. In the embodiment shown in FIG. 2A, the Tx MUTs 223 and the Rx MUTs 225 alternate in a way that creates minimum pitch in linear array configuration, thereby enabling better lateral resolution.

As will be described in further detail below, at any given time, a set of the Tx MUTs 223 can be selected for transmitting ultrasonic pulses, and a set of the Rx MUTs 225 can be selected for receiving echo pulses. For example, sets of Tx MUTs 223 that collectively make up rings can be used to form a quasi-annular array transducer, as will be described below with reference to FIGS. 3-5. Switches 222, which can be referred to as Tx switches 222, can be used to select which Tx MUTs 223 are active at a time. Similarly, switches 216, which can be referred to as Rx switches, can be used to select which Rx MUTs 225 are active at a time. In accordance with an embodiment, each of the Tx MUTs 223 is connected to a corresponding Tx switch. When the Tx switch is turned on (which can also be referred to as closed), the Tx MUT 223 is connected by its corresponding Tx switch to the HV pulser 224, thereby causing the Tx MUT 223 to output an ultrasonic pulse. When multiple MUTs 223 are triggered simultaneously (i.e., simultaneously connected by switches to the HV pulser 224), the multiple MUTs collectively produce an ultrasonic pulse or wave-front.

Selected Tx MUTs 223 transmit ultrasonic pulses into the target region being examined, and selected Rx MUTs 225 receive reflected ultrasonic pulses (i.e., "echo pulses") returning from the region. When transmitting, the selected Tx MUTs 223 are excited to high-frequency oscillation by the pulses emitted by the HV pulser 224, thereby generating ultrasound pulses that can be directed at a target region/object to be imaged.

These ultrasound pulses (also referred to as ultrasonic pulses) produced by the selected Tx MUTs 223 are echoed back towards the selected Rx MUTs 225 from some point within the target region/object, e.g., at boundary layers between two media with differing acoustic impedances. The echo pulses received by the selected Rx MUTs 225 are converted into corresponding low-level electrical input signals (i.e., the "echo signals") that are provided to the analog summing, amplification and processing circuitry 215. In specific embodiments, to receive echo pulses, the Rx switches 216 selectively connect a set of the Rx MUTs 225 to summing resistors 214, which are used to sum the echo pulses at the input of a summing amplifier 212.

FIG. 2B illustrates some further details of some of the blocks introduced in FIG. 2A, according to an embodiment of the present invention. Exemplary details of the Rx switches 216, the summing resistors 214 and the summing amplifier 212 are shown in FIG. 2B. The analog summing, amplification and processing circuitry 215 includes summing resistors 214 and a summing amplifier 212.

FIG. 2C illustrates a perspective view of the probe head assembly 105, according to an embodiment of the present invention. FIG. 2C also shows a portion of the interface cable 209, which is used to connect the components within the probe head assembly 105 to components within the probe housing 103.

FIG. 2D illustrates how odd and even rows can be staggered relative to one another. All of the rows and columns can be inline with one another, as shown in FIG. 2A. Alternatively, odd rows can be staggered relative even rows, as shown in FIG. 2D. It is also possible that odd columns be staggered relative to even columns. Other variations are also possible, and within the scope of an embodiment of the present invention. In the embodiments shown in FIGS. 2A, 3A and 3B, the Tx MUTs 223 and the Rx MUTs 225 alternate in a way that creates minimum pitch in linear array configuration, there by enabling better lateral resolution.

FIG. 3A is used to illustrate how sets of micromachined ultrasound transducers (MUTs) that collectively make up rings can be used to form a quasi-annular array transducer, and that such rings can be moved to emulate the mechanical movement of an annular array transducer, without requiring any moving parts. As mentioned above, sets of Tx MUTs 223 that collectively make up rings can be used to form a quasi-annular array transducer, as will now be described below with reference to FIGS. 3-5. Referring to FIG. 3A, illustrated therein are a plurality of possible MUT vectors, each of which is made up of a plurality of annular rings/circles of MUTs 221. Each such vector can be made up of a plurality of different sets of MUTs 221, wherein each set of MUTs defines a different annular ring/circle of MUTs 221, as can be appreciated from the discussion of FIGS. 4A-4D below.

Still referring to FIG. 3A, illustrated therein are four different MUT vectors, the first one of which is labeled Vector 1, and the last one of which is labeled Vector X. If, e.g., X=128, that would mean that 128 of the annular array MUT vectors can be produced using the MUT array 220. More specifically, by controlling the Tx and Rx switches 222 and 216 (in FIG. 2A), the various MUT Vectors (1 through 128) can be selected, one after the other, to emulate an annular array that is mechanically moved through 128 different physical positions. However, here there is no mechanical movement; but rather, different MUTs are selected to emulate the movement. FIG. 3B is a blown-up view of two of the closely spaced adjacent vectors shown in FIG. 3A.

FIG. 3B is a blown-up view of two of the vectors shown in FIG. 3A. As, shown, in the embodiments shown in FIGS. 3A and 3B, the Tx MUTs 223 and the Rx MUTs 225 alternate in a way that creates minimum pitch in linear array configuration, thereby enabling better lateral resolution.

FIGS. 4A-4D will now be used to illustrate how a transmit MUT vector can be used to transmit focused ultrasound beams. FIGS. 4A-4D are used to illustrate a transmit sequence, according to an embodiment of the present invention. FIGS. 4A-4D illustrates different sized rings of Tx MUTs 223, which can collectively be used to generate one focused ultrasound beam. More specifically, the ring of Tx MUTs shown in FIG. 4A can be used to collectively transmit a first ultrasound pulse; a short programmed delay thereafter the ring of Tx MUTs shown in FIG. 4B can be used to collectively transmit a second ultrasound pulse; a short programmed delay thereafter the ring of Tx MUTs shown in FIG. 4C can be used to collectively transmit a third ultrasound pulse; and a short programmed delay thereafter the ring of Tx MUTs shown in FIG. 4D can be used to collectively transmit a fourth ultrasound pulse. These four ultrasound pulses, as mentioned above, collectively make up a focused ultrasound beam.

The ring in FIG. 4A has the largest aperture, and the ring in FIG. 4D has the smallest/no aperture. In FIGS. 4A-4D, the four different rings shown therein do not overlap one another. However, in alternative embodiments, there can be overlap between the different rings. In other words, a Tx MUT can be included in more than one annular ring.

FIGS. 5A-5D illustrate how a receive MUT vector can be used to receive echo pulses generated in response to the focused ultrasound beam FIGS. 5A-5D illustrate different sized rings of Rx MUTs 225, which can collectively be used to receive echo pulses and produce an echo signal. More specifically, the ring of Rx MUTs 225 shown in FIG. 5A can be used to collectively receive a first echo pulse; a short programmed delay thereafter the ring of Rx MUTs shown in FIG. 5B can be used to collectively receive a second echo pulse; a short programmed delay thereafter the ring of Rx MUTs shown in FIG. 5C can be used to collectively receive a third echo pulse; and a short programmed delay thereafter the ring of Rx MUTs shown in FIG. 5D can be used to collectively receive a fourth echo pulse. These four echo pulses collectively make up a received ultrasound echo.

Figure 5A:
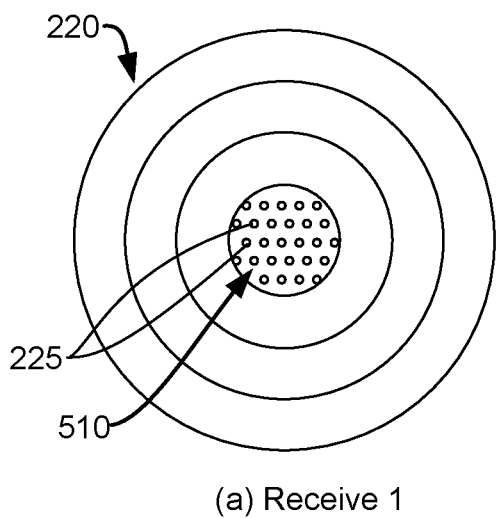
FIGS. 5A-5D are used to illustrate a receive sequence, according to an embodiment of the present invention.
Figure 5B:
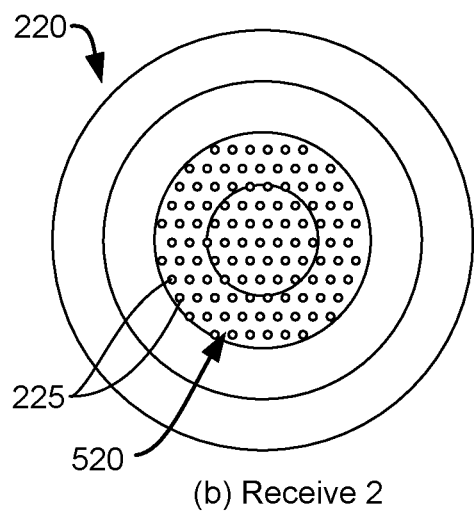
Figure 5C:
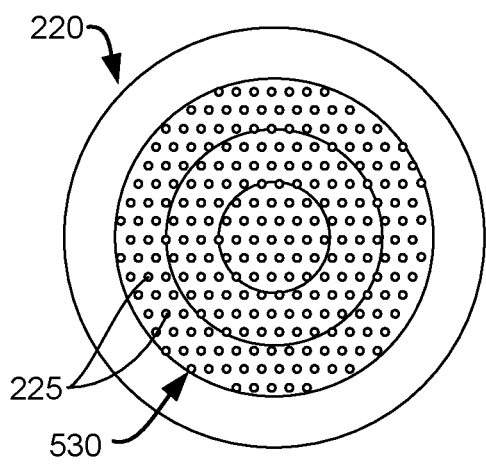
Figure 5D:
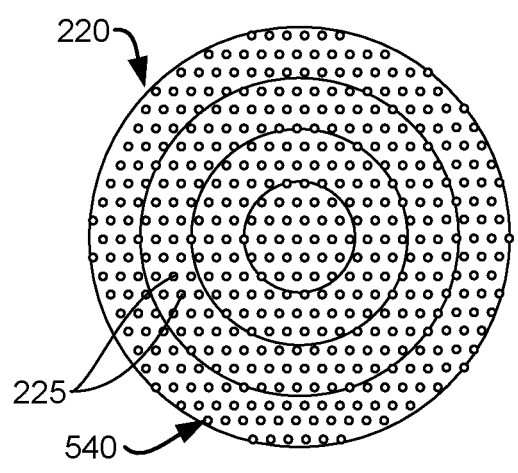

The circle of Rx MUTs in FIG. 5A, which has the smallest aperture, will receive near field echoes. By contrast, the circle of Rx MUTs in FIG. 5D, which has the largest aperture, will receive the deepest field echoes. In FIGS. 5A-5D, the four different circles shown therein overlap one another. Further, it is noted that sets of the Rx MUTs can be selected in such a way that the active area of the circular arrays can continuously increase with a controlled number of sampling cycles in order to optimize the resolution of the received signal from different depths.

In accordance with certain embodiments of the present invention, preprogrammed vector configuration and timing data that enables the various annular rings shown in FIGS. 4A-4D to be fired in sequence is stored in the memory 230, e.g., in a LUT. Similar data used the controls reception, as was described with reference to FIGS. 5A-5D, is also stored in the memory 230. Advantageously, the MUT array 220 and the circuitry used to select sets of the MUTs can provide a continuously variable aperture annular array. More specifically, such circuitry can be used to activate sets of MUTs in such a way that the active area of annular arrays will continuously shift in order to form ultrasound beams with variable focal points. In other words, the MUT array 220 can be used to perform beam forming and aperture control for each of a plurality of different MUT vectors. Advantageously, beam shapes can be optimized for both transmit and receive signals.

While the Tx MUT and Rx MUT vectors shown in FIGS. 4A-4D and 5A-5D include substantially circular annular arrays, because of the flexibility provided by the MUT array 220, the vectors can have alternative shapes, such as, but not limited to elliptical shapes. In alternative embodiments, the Tx MUTs and Rx MUTs can be selectively connected to produce other types of arrays, besides annular arrays.

In alternative embodiments, rather than having half the MUTs 221 dedicated to functioning as Tx MUTs 223, and half the MUTs 221 dedicating to functioning as Rx MUTs 225, each of the MUTs 221 of the MUT array 220 can be capable of being used as either an Rx MUT 223 or a Tx MUT 225. In such alternative embodiments, transmit/receive (Tx/Rx) switches can be used in place Tx switches 222 and the Rx switches 216, and the Tx/Rx switches can be used to connect a selected set of the MUTs to either the pulser 224 or the analog summing, amplification and processing circuitry 215. When a high voltage pulse is produced by the pulser 224, the Tx/Rx switches would automatically block the high voltage from damaging the analog summing, amplification and processing circuitry 215. When the HV pulser 224 is not producing a pulse, the Tx/Rx switches would disconnect the selected set of MUTs from the pulser 224, and to connect the selected set of MUTs to the analog summing, amplification and processing circuitry 215. However, the aforementioned embodiments where certain MUTs are dedicated to transmission, and other MUTs are dedicated to reception, such a configuration eliminates the need Tx/Rx switches, which are relatively expensive.

The foregoing description of preferred embodiments of the present invention has been provided for the purposes of illustration and description. It is not intended to be exhaustive or to limit the invention to the precise forms disclosed. Many modifications and variations will be apparent to one of ordinary skill in the relevant arts. The above mentioned part numbers are exemplary, and are not meant to be limiting. Accordingly, other parts can be substituted for those mentioned above.

The embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the claims and their equivalents.

What is claimed is:

1. An ultrasound system comprising:
    a portable ultrasound imaging probe;
    a probe head mounted on the probe including an array comprising a plurality of ultrasound transmitting ultrasound transducers (Tx transducers) and a plurality of ultrasound receiving ultrasound transducers (Rx transducers);
    a high voltage (HV) pulser within the probe;
    an analog summing amplifier within the probe;
    a plurality of transmit (Tx) switches within the probe, wherein each of the plurality of Tx switches connects the HV pulser and a different one of the plurality of Tx transducers;
    a plurality of receive (Rx) switches within the probe, wherein each of the plurality of Rx switches connects a different one of the plurality of Rx transducers to the analog summing amplifier;
    wherein the plurality of Tx switches is not connected to the plurality of Rx transducers, and the plurality of Rx switches is not connected to the plurality of Tx transducers whereby the Rx transducers are never used to emit ultrasound;
    a controller within the probe and coupled to the plurality of Tx switches and plurality of Rx switches;
    wherein the controller is configured to selectively close the Tx switches to connect transmit sets of the Tx transducers to the HV pulser including a first transmit set of the transmit sets of the Tx transducers at a first transmit time, a second transmit set of the transmit sets of the Tx transducers at a second transmit time, and a third transmit set of the transmit sets of the Tx transducers at a third transmit time; and the controller is configured to selectively close the Rx switches to connect receive sets of the Rx transducers to the analog summing amplifier including a first receive set of the receive sets of the Rx transducers at a first receive time, a second receive set of the receive sets of the Rx transducers at a second receive time, and a third receive set of the receive sets of the Rx transducers at a third receive time;
    wherein the analog summing amplifier combines echoes detected by the receive sets of ultrasound transducers into an analog echo signal which is output by the analog summing amplifier;
    an analog-to-digital converter (ADC) within the probe that converts the analog echo signal output by the analog summing amplifier, to a digital echo signal;
    an interface cable configured to connect the probe to a host computer; and
    interface circuitry within the probe that transfers the digital echo signal through the interface cable to the host computer.

2. The ultrasound system of claim 1, wherein the probe consumes at most 2.5 Watts of power.

3. The ultrasound system of claim 1, wherein:
    the first transmit set of Tx transducers is at a first position within said array, the second transmit set of Tx transducers is at a second position within said array, and the third transmit set of Tx transducers is at a third position within said array, such that the probe head emits an ultrasound beam from the first position within the array at the first time, the second position within the array at the second time, and the third position within the array at the third time without moving the probe head.

4. The ultrasound system of claim 1, wherein:
    the first receive set of Rx transducers is at a first position within said array, the second transmit set of Rx transducers is at a second position within said array, and the third receive set of Rx transducers is at a third position within said array, such that the probe head receives ultrasound echoes from the first position within the array at the first time, the second position within the array at the second time, and the third position within the array at the third time without moving the probe head.

5. The ultrasound system of claim 1, wherein:
    the first transmit set of Tx transducers have a first annular distribution within said array, the second transmit set of Tx transducers have a second annular distribution within said array having a smaller aperture than the first transmit set of Tx transducers, and the third transmit set of Tx transducers have a third annular distribution within said array having a smaller aperture than the second transmit set of Tx transducers; and
    whereby the array of ultrasound transducers operates as a variable aperture ultrasound transmitter.

6. The ultrasound system of claim 1, wherein:
    the first set Rx transducers is smaller than the second set of Rx transducers, which is smaller than the third set of Rx transducers, such that the set of Rx transducers connected to the analog summing, amplification and signal processing circuitry increases in size over time;
    whereby the array of ultrasound transducers operates as a variable aperture ultrasound receiver.

7. The ultrasound system of claim 1, wherein:
    the first receive set of Rx transducers have a first circular distribution within said array, the second receive set of Rx transducers have a second circular distribution within said array having a larger diameter than the first receive set of Rx transducers, and the third receive set of Rx transducers have a third circular distribution within said array having a larger diameter than the second receive set of Rx; transducers, in order to enhance resolution of ultrasound echoes from different depths.

8. The ultrasound system of claim 1, further comprising the host computer connected to the probe by the interface cable wherein:
    the host computer receives the digital echo signal from the interface circuitry; and
    wherein the host computer is configured to perform digital processing of the digital echo signal received from the probe and display ultrasound images on a display associated with the host computer.

9. The ultrasound system of claim 1, further comprising the host computer connected to the probe by the interface cable wherein:
the host computer provides power to operate the probe via the interface cable;
the host computer receives the digital echo signal from the interface circuitry; and
wherein the host computer is configured to perform digital processing of the digital echo signal received from the probe and display ultrasound images on a display associated with the host computer.

10. The ultrasound system of claim 1, wherein:
the controller is configured to selectively close the Tx switches to connect transmit sets of the Tx transducers to the HV pulser and close the Rx switches to connect receive sets of the Tx transducers to the analog summing amplifier using vector configuration and timing data stored within a memory within the probe.

11. The ultrasound system of claim 10, in combination with the host computer connected to the probe by the interface cable wherein:
the host computer is configured to send instructions to the probe via the interface cable that cause the controller to select, from the memory, specific vector configuration and timing data to control transmitting and receiving of ultrasound by the probe.

12. The ultrasound system of claim 10, in combination with the host computer connected to the probe by the interface cable wherein:
the host computer is configured to write vector configuration and timing data to the memory via the interface cable.

13. The ultrasound system of claim 1, wherein the Tx transducers and the Rx transducers comprise micro-machined ultrasound transducers (MUTs) machined in rows and columns on a common substrate to form the array.

14. An ultrasound system comprising:
a portable ultrasound imaging probe;
a probe head mounted on the probe including an array comprising a plurality of ultrasound transmitting ultrasound transducers (Tx transducers) and a plurality of ultrasound receiving ultrasound transducers (Rx transducers);
a high voltage (HV) pulser within the probe;
an analog summing amplifier within the probe;
a plurality of transmit (Tx) switches within the probe, wherein each of the plurality of Tx switches is connected between the HV pulser and a different one of the plurality of Tx transducers;
a plurality of receive (Rx) switches within the probe, wherein each of the plurality of Rx switches is connected between a different one of the plurality of Rx transducers and the analog summing amplifier;
wherein the plurality of Rx switches and Rx transducers are isolated from the HV pulser and are never used to emit ultrasound;
a controller within the probe and coupled to the plurality of Tx switches and plurality of Rx switches;
wherein the controller is configured to selectively close the Tx switches to connect transmit sets of the Tx transducers to the HV pulser including a first transmit set of the transmit sets of the Tx transducers at a first transmit time, a second transmit set of the transmit sets of the Tx transducers at a second transmit time, and a third transmit set of the transmit sets of the Tx transducers at a third transmit time; and the controller is configured to selectively close the Rx switches to connect receive sets of the Rx transducers to the analog summing amplifier including a first receive set of the receive sets of the Rx transducers at a first receive time, a second receive set of the receive sets of the Rx transducers at a second receive time, and a third receive set of the receive sets of the Rx transducers at a third receive time;
wherein the analog summing amplifier combines echoes detected by the receive sets of ultrasound transducers into an analog echo signal which is output by the analog summing amplifier;
an analog-to-digital converter (ADC) within the probe that converts the analog echo signal output by the analog summing amplifier, to a digital echo signal;
an interface cable; and
interface circuitry within the probe that transfers the digital echo signal through the interface cable.

15. The ultrasound system of claim 14, wherein the probe consumes at most 2.5 Watts of power.

16. The ultrasound system of claim 14, wherein:
the controller is configured to selectively close the Tx switches to connect transmit sets of the Tx transducers to the HV pulser and close the Rx switches to connect receive sets of the Tx transducers to the analog summing amplifier using vector configuration and timing data stored within a memory within the probe.

17. The ultrasound system of claim 14, further comprising a host computer connected to the probe by the interface cable wherein:
the host computer receives the digital echo signal from the interface circuitry; and
wherein the host computer is configured to perform digital processing of the digital echo signal received from the probe and display ultrasound images on a display associated with the host computer.

18. The ultrasound system of claim 17 wherein:
the host computer is further configured to send instructions to the probe via the interface cable that cause the controller to select, from the memory, specific vector configuration and timing data to control transmitting and receiving of ultrasound by the probe.

19. The ultrasound system of claim 17 wherein:
the host computer is further configured to write vector configuration and timing data to the memory via the interface cable.

20. The ultrasound system of claim 17 wherein:
the host computer provides power to operate the probe via the interface cable.

21. The ultrasound system of claim 14, wherein:
the first transmit set of Tx transducers is at a first position within said array, the second transmit set of Tx transducers is at a second position within said array, and the third transmit set of Tx transducers is at a third position within said array, such that the probe head emits ultrasound from the first position within the array at the first time, the second position within the array at the second time, and the third position within the array at the third time without moving the probe head.

22. The ultrasound system of claim 14, wherein:
the first receive set of Rx transducers is at a first position within said array, the second transmit set of Rx transducers is at a second position within said array, and the third receive set of Rx transducers is at a third position within said array, such that the probe head receives ultrasound echoes from the first position within the array at the first time, the second position within the array at the second time, and the third position within the array at the third time without moving the probe head.

23. The ultrasound system of claim 14, wherein:
the first transmit set of Tx transducers have a first annular distribution within said array, the second transmit set of Tx transducers have a second annular distribution within said array having a smaller aperture than the first transmit set of Tx transducers, and the third transmit set of Tx transducers have a third annular distribution within said array having a smaller aperture than the second transmit set of Tx transducers; and
whereby the array of ultrasound transducers operates as a variable aperture ultrasound transmitter.

24. The ultrasound system of claim 14, wherein:
the first set Rx transducers is smaller than the second set of Rx transducers, which is smaller than the third set of Rx transducers, such that the set of Rx transducers connected to the analog summing, amplification and signal processing circuitry increases in size over time; whereby the array of ultrasound transducers operates as a variable aperture ultrasound receiver.

25. The ultrasound system of claim 14, wherein:
the first receive set of Rx transducers have a first circular distribution within said array, the second receive set of Rx transducers have a second circular distribution within said array having a larger diameter than the first receive set of Rx transducers, and the third receive set of Rx transducers have a third circular distribution within said array having a larger diameter than the second receive set of Rx; transducers, in order to enhance resolution of ultrasound echoes from different depths.

26. The ultrasound system of claim 14, wherein the Tx transducers and the Rx transducers comprises micro-machined ultrasound transducers (MUTs) machined in rows and columns on a common substrate.

* * * * *